United States Patent [19]

Davidonis et al.

[11] Patent Number: 5,573,941
[45] Date of Patent: Nov. 12, 1996

[54] CALLUS FORMATION VANILLA PLANIFOLIA

[75] Inventors: Gayle Davidonis, Metairie, La.; Dietrich W. Knorr, Newark; Lynn G. Romagnoli, Greenville, both of Del.

[73] Assignee: University of Delaware, Newark, Del.

[21] Appl. No.: 136,091

[22] Filed: Oct. 14, 1993

Related U.S. Application Data

[63] Continuation of Ser. No. 745,783, Aug. 16, 1991, abandoned, which is a continuation of Ser. No. 353,282, May 17, 1989, abandoned, which is a continuation-in-part of Ser. No. 169,639, Mar. 17, 1988, abandoned, which is a continuation-in-part of Ser. No. 169,641, Mar. 17, 1988, abandoned.

[51] Int. Cl.$^6$ .............................. C12N 5/04; A01H 4/00; C12P 1/00
[52] U.S. Cl. ................. 435/240.4; 435/240.48; 435/240.49; 435/156
[58] Field of Search ................. 435/240.4, 240.48, 435/156, 240.49

[56] References Cited

U.S. PATENT DOCUMENTS

| | | | |
|---|---|---|---|
| 1,010,043 | 11/1911 | Gowen | 426/534 |
| 3,112,204 | 11/1963 | Yanick | 426/534 |
| 5,057,424 | 10/1991 | Knuth et al. | 435/240.48 |
| 5,068,184 | 11/1991 | Knuth et al. | 435/41 |
| 5,262,315 | 11/1993 | Gross et al. | 435/147 |
| 5,279,950 | 1/1994 | Labuda et al. | 435/147 |

FOREIGN PATENT DOCUMENTS 8900820  2/1989  WIPO.

OTHER PUBLICATIONS

Romagnoli et al 1988 Food Biotechnology 2(1):93–104.
Cheetham 1993 Trends in Biotechnology 11: 478–488.
Chen et al 1988 (May) Applied Environ. Microbiol. 54(5): 1254–1257.
Rahouti et al 1989 (Sep.) Applied Environ. Microbiol 55(9):2391–2398.
Funk et al 1990 (Mar.) Phytochemistry 29(3):845–848.
Westcott et al 1994 Phytochemistry 35(1):135–138.
Jarrett et al 1984 Plant Genetics Resources Newsletter 57:25–27.
Gamborg et al 1981 In Plant Tissue Culture; Thorpe (ed.); Academic Press NY pp. 21, 26, and 27.
Flick et al 1983 In Handbook of Plant Cell Culture vol. 1; Evans et al (ed); MacMillan Publ Co. NY pp. 64–65.
Merck–Index 1983 Tenth Edition; Merck & Co; Rahway NY, p. 1419 entry No. 9734.
Kurz et al 1979 Adv Appl Microbiol 25:209–240.
Evans et al 1981 In Plant Tissue Culture; Thorpe (ed); Academic Press NY pp. 51–52.
Torssell 1983 In Natural Product Chemistry; Wiley & Sons Limited NY pp. 82 and 85.
Sahai et al 1986 The World Biotech Report 2:71–85.

*Primary Examiner*—Patricia R. Moody
*Attorney, Agent, or Firm*—Donald W. Huntley

[57] ABSTRACT

Described and claimed are the callus of *Vanilla planifolia*, the preparation of the same and the extraction of vanillin therefrom, and the use of ferulic acid to increase the content of vanillin.

11 Claims, No Drawings

CALLUS FORMATION VANILLA PLANIFOLIA

RELATED APPLICATIONS

This is a continuation, of application Ser. No. 07/745,783 filed Aug. 16, 1991, now abandoned, which is a continuation of U.S. application Ser. No. 07/353,282, filed May 17, 1989, and now abandoned itself a continuation-in-part of U.S. applications Ser. No. 07/169,639 and Ser. No. 07/169,641, both filed Mar. 17, 1988, and both now abandoned.

BACKGROUND OF THE INVENTION

1. Field of the Invention

This invention relates to the mass of undifferentiated cells termed callus of the vanilla-producing orchid *Vanilla planifolia* and has as its principal object provision of a reliable method for producing the same. It also provides utilities of the callus as a source for regenerating the orchids and as a source of vanillin.

2. Prior Art

*Vanilla planifolia*, a monopodial orchid usually propagated by cuttings, is the natural source of vanilla flavoring.

Recently, two tissue culture methods of propagation of this orchid have been reported using (1) nodal segments (Cervera et al. (1981) In vitro propagation of vanilla (*Vanilla planifolia* A.) Environ. Expt. Bot. 21:441 (Abst.); Kononowicz et al. (1984) In vitro propagation of *Vanilla planifolia*. Hortscience 19:58–59) or (2) aerial root tips (Philip et al. (1986) Clonal propagation of *Vanilla planifolia* (Salisb.) Ames using tissue culture. *J. Plant Physiol.* 122:211–215).

The status of callus of the orchid is somewhat obscure. Unsuccessful attempts to induce formation of the callus have been reported (Kononowicz et al., op. cit.). Other investigators mention callus: see Sahai et al., Producing high value food ingredients via plant biotechnology, The World Biotech Report 1980, Vol. 2, Part 1, pp. 71–85. Jarret et al., (1984) *Shoot-Tip Vanilla Culture for Storage and Exchange, Plant Genetic Resources Newsletter* 57:25–27, note the formation of callus without giving any properties. At any rate, there has heretofore been no reliable method of producing callus.

DESCRIPTION OF THE INVENTION

In accordance with the present invention, callus of the orchid *Vanilla planifolia* is initiated and grown by a process in which explants from aseptic shoots of the orchid are maintained in the dark on a callus proliferation medium consisting of an agar-solidified solution of Murashige and Skoog basal salts supplemented with certain growth hormones, sucrose and vitamins. This medium can be used to grow vanilla plants from vanilla explants when maintained in the light.

In practice, a commercial preparation of MS basal salts (Hazleton Research Products, Lenaxa, Kans.) was used to form the culture medium. The salts are described by Murashige and Skoog, "A revised medium for rapid growth and bioassays with tobacco tissue cultures," *Physiol Plant.* 15:473–497 (1962), and consist of the following:

| Commercial Aqueous Murashige and Skoog Basal Salt Solution Without Agar | |
|---|---|
| Component | mg/liter of $H_2O$ |
| $NH_4NO_3$ | 1650.00 |
| $KNO_3$ | 1900.000 |
| $CaCl_2$ (Anhydrous) | 333.000 |
| $MgSO_4$ (Anhydrous) | 181.000 |
| $KH_2PO_4$ | 170.000 |
| FeNaEDTA | 36.700 |
| $H_3BO_3$ | 6.200 |
| $MnSO_4 \cdot H_2O$ | 16.900 |
| $ZnSO_4 \cdot 7H_2O$ | 8.600 |
| KI | .830 |
| $Na_2MoO_4 \cdot 2H_2O$ | 2.500 |
| $CuSO_4 \cdot 5H_2O$ | .025 |
| $CoCl_2 \cdot 6H_2O$ | .025 |
| Total | 4303.530 |

Selected auxin and cytokinin growth regulators were included as supplements. Effective auxins are α-naphthaleneacetic acid and 2,4-dichlorophenoxacetic acid in a concentration of up to about 5 mg/l and indole-3-acetic acid in a concentration of 10–30 mg/l. Effective cytokinins, are 6-benzylaminopurine (also known as benzyladenine) and 6-[γ,γ-dimethylallylamino]purine in a concentration of up to about 3 mg/l. In general, these regulators (auxins or cytokinins) are effective in the range 0.01–6 mg/l and above per liter of medium. The regulators may be used alone or in admixture.

The commercial solution was also supplemented with:

| Component | g (or mg)/l |
|---|---|
| Sucrose | 20–40 |
| Casein hydrolysate | 0–500 (mg/l) |
| Thiamine hydrochloride | 0–10 (mg/l) |
| Myo-inositol | 0–1000 (mg/l) |

The acidity of the supplemented solution was adjusted, as necessary, to pH 5.6–5.9 by addition of 0.1N NaOH, 5–10 g/l of agar was added at room temperature, and the solution was autoclaved and allowed to solidify.

Explants of *Vanilla planifolia* were placed on the solidified medium and maintained in darkness at 26° C. Development of callus began in about two weeks.

The commercial medium as used above can be used for regenerating adventitious shoots from callus. The callus need only be placed in light to develop into completely differentiated plants.

In addition to serving as progenitors of whole *Vanilla planifolia* plants, the callus is also useful as a source of vanillin and other flavor components. These substances can readily be extracted from the callus by an effective organic solvent such as ethyl alcohol, chloroform or ether. The process is similar to that used with vanilla beans.

The quantity of vanillin produced by the callus can be increased by treating the callus with ferulic acid. For example, when ferulic acid in a concentration of about 1 mM/l (=millimole/liter; 1 mM=0.1941 g of ferulic acid here) is supplied to growing *Vanilla planifolia* callus in darkness, the vanillin content of the callus increases. Without added ferulic acid, vanillin content increases 1.2-fold over a 30-day growth period. With 1 mM/l of ferulic acid, the vanillin increases 1.7-fold over the same growth period. The callus turns brown when the concentration of ferulic acid reaches about 10 mM/l and vanillin production ceases.

In practice, the ferulic acid solutions were applied topically to pieces of callus in a ratio of 100 μl of 1 mM solution per 0.1 g of callus tissue, but other methods of supply of ferulic acid can undoubtedly be used as well, e.g., by adding ferulic acid to the liquid or solid nutrient medium.

There follow some examples illustrating the invention in detail.

EXAMPLE 1

GROWTH OF CALLUS

A. Growth of Shoots from Explants

Shoots of *Vanilla planifolia* were obtained from J. Janick at Purdue University.

Primarily in order to secure plants decontaminated from microorganisms, shoots were surface sterilized by treatment for 30 minutes in hydrogen peroxide (30%), rinsing in sterile distilled water, treatment in a 20% commercial bleach ("CLOROX" sodium hypochlorite solution) for 30 minutes, and rinsing again in sterile distilled water. Shoot explants approximately 2 inches long were cut and placed on a medium consisting of (pH 5.8) commercial Murashige and Skoog basal salts (see table above). The medium also contained (1) 0.4 mg/l of 6-benzylaminopurine, (2) 1.0 mg/l of 6-benzylaminopurine, or (3) 2-mg/l of α-naphthaleneacetic acid plus 1 mg/l of 6-benzylaminopurine, and was solidified with 10 mg/l of acetone-washed agar. The temperature was maintained at 26° C. and illumination was supplied at $4.5\mu$ E./m$^2$/sec for at least 45 days.

B. Development of Callus

After 45 days, aseptic shoot tips (2 cm) were sectioned into 1–2 mm disks and placed on hardened callus proliferation media held in compartmentalized petri dishes. The media contained commercial Murashige and Skoog salts (see table) supplemented with 5 mg/l of thiamine hydrochloride, 1000 mg/l of myo-inositol, 500 mg/l of casein hydrolysate, 30 g/l of sucrose and 7.5 g/l of agar and (1) 4 mg/l of α-napthaleneacetic acid, 2 mg/l of 6-benzylaminopurine or (2) 2 mg/l of α-naphthaleneacetic acid plus 1 mg/l of 6-benzylaminopurine. The petri dishes with shoot explants were maintained in the dark at 26° C. Initiation of callus was found to begin on some shoots at the end of two weeks under these conditions. Stock callus cultures have subsequently been maintained on callus proliferation media at 26° C. in the dark for 2½ years.

EXAMPLE 2

GENERATION OF PLANTS FROM CALLUS

Callus as produced above can be used to regenerate shoots of the vanilla plant by exposure to light.

Callus was transferred to media containing Murashige and Skoog salts supplemented with 500 mg/l of casein hydrolysate and (1) 2 mg/l of α-naphthaleneacetic acid, (2) 2 mg/l of α-naphthaleneacetic acid plus 0.1 mg/l of 6-benzylaminopurine, (3) 0.2 mg/l of α-naphthaleneacetic acid, (4) 0.1 mg/l of 6-benzylaminopurine, or (5) 0.2 mg/l of α-naphthaleneacetic acid plus 1 mg/l of 6-benzylaminopurine. The callus, in 125 ml Erlenmeyer flasks, was placed in the light at 26° C. and transferred to a fresh medium every two weeks. The flasks were examined after six weeks and shoots were found on the callus.

EXAMPLE 3

VANILLIN AND ADDITION OF FERULIC ACID TO CALLUS

*Vanilla planifolia* callus was grown in darkness at about 26° C. on a callus proliferation medium of Murashige and Skoog salts containing 5 mg/l of thiamine hydrochloride, 1000 mg/l of inositol, 300 mg/l of casein hydrolysate, 2 mg/l of α-naphthaleneacetic acid and 1 mg/l of benzyladenine at pH 5.8 hardened with 7.5 g/l of agar.

Ferulic acid (Sigma) solutions of 1 mM and 10 mM were prepared and filter-sterilized (Nalgene Disposable Filterware, 115 ml, 2 micron). Respective solutions were applied under sterile conditions in a laminar flow hood (Model 760, Contamination Control Inc., Lansdale, Pa.) with a Pipetman (P1000 Rainin Instrument Co., Inc.) to 7 preweighed callus pieces in a ratio of 100 μl of one mM solution per 0.1 g of callus tissue. The callus pieces were held in fresh callus proliferation medium in compartmentalized petri dishes. Experiments with both 1 mM and 10 mM solutions were repeated in triplicate.

Over a 28-day period, callus pieces were sacrificed and the vanillin extracted therefrom with alcohol and water. Vanillin concentration was determined by high pressure liquid chromatography.

The vanillin concentration in a control sample (without ferulic acid addition) increased from 1.83 μg/g fresh weight (f.w.) to 2.20 μg/g f.w., a 1.2-fold increase, over a 28-day growth period. Samples treated with ferulic acid had a vanillin concentration increase from 4.43 μg/g f.w. to 7.40 μg/g f.w., a 1.7-fold increase over 28 days.

The samples treated with a concentration of 10 mM turned brown, and the vanillin content decreased.

Having described our invention,

We claim:

1. The process of increasing the quantity of vanillin produced by *Vanilla plainifolia* callus derived from shoot tissue which comprises supplying to the same a ferulic acid solution having a concentration of about 1 mM of ferulic acid.

2. A process of claim 1 further comprising extracting the vanillin by contacting the callus with solvent for vanillin.

3. A process of claim 2 wherein the solvent is ethanol.

4. A process of claim 1 wherein the ferulic acid is applied topically to the callus.

5. A process of claim 1 wherein the ferulic acid solution is supplied to the callus for a period of about 28 days.

6. A process of claim 1 wherein the *Vanilla plainifolia* callus was grown in darkness.

7. The process of claim 1 wherein the callus of the orchid *Vanilla plainifolia* is grown by incubating an explant of the *Vanilla plainifolia* plant in darkness on an agar-solidified basal salt medium containing an effective amount of an effective growth hormone at about room temperature and harvesting the resulting callus.

8. The process of claim 7 wherein the growth hormone is α-naphthaleneacetic acid.

9. The process of claim 7 wherein the growth hormone is 6-benzylaminopurine.

10. The process of claim 7 wherein the growth hormone is indole-3-acetic acid.

11. The process of claim 7 wherein the growth hormone is 6-(γ,γ-dimethylallylamino)purine.

* * * * *